(12) United States Patent
Na et al.

(10) Patent No.: US 12,195,760 B2
(45) Date of Patent: *Jan. 14, 2025

(54) METHOD FOR ENHANCING PROLIFERATION CAPABILITY OF STEM CELLS USING ETHIONAMIDE

(71) Applicant: SAMSUNG LIFE PUBLIC WELFARE FOUNDATION, Seoul (KR)

(72) Inventors: Duk Lyul Na, Seoul (KR); Jong Wook Chang, Seoul (KR); Hyo Jin Son, Seoul (KR); Su Hyeon Myeong, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 79 days.

This patent is subject to a terminal disclaimer.

(21) Appl. No.: 18/152,464

(22) Filed: Jan. 10, 2023

(65) Prior Publication Data

US 2023/0146610 A1     May 11, 2023

Related U.S. Application Data

(63) Continuation of application No. 16/627,875, filed as application No. PCT/KR2017/010772 on Sep. 28, 2017, now abandoned.

(30) Foreign Application Priority Data

Oct. 24, 2016   (KR) .................. 10-2016-0138657
Sep. 27, 2017   (KR) .................. 10-2017-0125324

(51) Int. Cl.
    *C12N 5/00*       (2006.01)
    *C12N 5/0775*     (2010.01)

(52) U.S. Cl.
    CPC ...... *C12N 5/0665* (2013.01); *C12N 2501/999* (2013.01)

(58) Field of Classification Search
    CPC .................. C12N 5/0665; C12N 2501/999
    See application file for complete search history.

(56) References Cited

U.S. PATENT DOCUMENTS 11,913,020 B2 *   2/2024   Na et al. .............. C12N 5/0606
11,946,070 B2 *   4/2024   Na et al. .............. C12N 5/0606

FOREIGN PATENT DOCUMENTS

| KR | 10-2011-0072839 A | 6/2011 | |
| KR | 10-2011-0085231 A | 7/2011 | |
| KR | 10-2015-0004762 A | 1/2015 | |
| WO | WO 2015/009884 A1 * | 1/2015 | ........... C12N 5/0775 |

OTHER PUBLICATIONS

Wang et al. (2012) "Comparison of endometrial regenerative cells and bone marrow stromal cells" Journal of Translational Medicine, 10:207, 14 pages. (Year: 2012).*

Katrahalli, U., et al. (2012) "The effect of anti-tubercular drug, ethionamide on the secondary structure of serum albumins: a biophysical study." *J Pharm Biomed Anal.*, 59:102-8, (Feb. 5, 2012).

International Search Report dated Jan. 16, 2018, issued in International Patent Application No. PCT/KR2017/010772, with English translation.

Peng et al. (Dec. 18, 2015) "Suppression of N RF2-ARE activity sensitizes chemotherapeutic agent-induced cytotoxicity in human acute monocytic leukemia cells" Toxicology and Applied Pharmacology, 292, 1-7. (Year: 2015).

Office Action (Non-Final) from corresponding U.S. Appl. No. 16/627,875, dated Jun. 1, 2022.

Office Action (Final) from corresponding U.S. Appl. No. 16/627,875, dated Oct. 14, 2022.

Advisory Action from corresponding U.S. Appl. No. 16/627,875, dated Jan. 3, 2023.

* cited by examiner

*Primary Examiner* — Teresa E Knight
*Assistant Examiner* — James Joseph Graber
(74) *Attorney, Agent, or Firm* — Harness, Dickey & Pierce, P.L.C.

(57) ABSTRACT

The present disclosure relates to a medium composition for enhancing proliferation of stem cells, comprising ethionamide, and a use thereof. It is possible, according to the present disclosure, to mass-produce highly-efficient next-generation stem cells through a simple and safe method of controlling a culturing environment, without using genetic modification or viral vectors, etc.

2 Claims, 7 Drawing Sheets

Osteogenesis

Control

Ethionamide-primed MSCs

METHOD FOR ENHANCING PROLIFERATION CAPABILITY OF STEM CELLS USING ETHIONAMIDE

CROSS-REFERENCE TO RELATED APPLICATIONS

This application is a continuation application of U.S. patent application Ser. No. 16/627,875, filed on 31 Dec. 2019, which is national phase application of PCT Application No. PCT/KR2017/010772, filed 28 Sep. 2017, which claims benefit of Korean Patent Application No. 10-2017-0125324, filed on Sep. 27, 2017 and Korean Patent Application No. 10-2016-0138657, filed on Oct. 24, 2016. The entire disclosures of the applications identified in this paragraph are incorporated herein by references.

FIELD

The present disclosure relates to a medium composition for enhancing the proliferation of stem cells, including ethionamide, and a use thereof.

BACKGROUND

As mesenchymal stem cells are known to be cells that maintain their multipotency and participate in tissue regeneration, treatment, and immune responses, an effort has been made to develop therapeutic agents for various diseases by separating mesenchymal stem cells from umbilical cord blood, bone marrow, and the like and culturing the mesenchymal stem cells, using such characteristics. However, the stem cells have a problem in that the stem cells lose their stemness because their aging progresses and their cell differentiation occurs as they are sub-cultured.

That is, to develop a cell therapeutic agent using adult stem cells without ethical issues, it is essential to establish a method capable of effectively proliferating adult stem cells while maintaining the stemness of the adult stem cells. However, the adult stem cells have a drawback in that they have a low proliferation rate and are easily aged, resulting in a limited number of cells that may be obtained from one tissue.

As a plan to solve these problems to enhance the efficiency of the stem cells, a genetic modification method using a viral vector or a method of over-expressing a certain protein has been proposed (Registered Korean Patent No. 10-1101835), but such a method has a drawback in that it is difficult to apply it to clinical studies due to its stability issue. Although the method has a proven probability of clinical application to treat a certain disease by means of first-generation research on stem cells, it has low efficiency and a poorly identified mechanism of action, and also has no solution to ensure safety.

In this regard, it was recently reported that the glycolytic metabolism increases and the oxidative phosphorylation metabolism decreases in embryonic stem cells (ESCs) and induced pluripotent stem cells (iPSs), compared to differentiated cells, suggesting that there is a chance of developing high-efficiency stem cells by maintaining the stemness of the stem cells and suppressing cell aging through reprogramming for regulating the metabolic processes. However, little is known about a molecular biological mechanism for this and effective regulation technology remains to be developed.

SUMMARY

Technical Problem

Accordingly, the present inventors have conducted intensive research on a method capable of suppressing the aging of stem cells and enhancing cell survival and proliferation rates, and found that ethionamide known as a conventional antibiotic can effectively proliferate stem cells. Therefore, the present disclosure has been completed based on these facts.

Therefore, it is an object of the present disclosure to provide a medium composition for enhancing the survival/proliferation of stem cells, which includes ethionamide, and a use thereof.

However, the technical objects of the present disclosure are not limited thereto, and other objects of the present disclosure which are not stated herein will become more apparent to those of ordinary skill in the art by describing in detail exemplary embodiments thereof.

Technical Solution

One aspect of the present disclosure provides a medium composition for enhancing the proliferation of stem cells, which includes ethionamide.

According to one embodiment of the present disclosure, the ethionamide may be included at a concentration of 1 to 500 μM in a medium.

According to another embodiment of the present disclosure, the medium may be an α-minimum essential media (α-MEM) medium supplemented with fetal bovine serum (FBS) and gentamicin.

According to still another embodiment of the present disclosure, the stem cells may be embryonic stem cells or adult stem cells.

According to yet another embodiment of the present disclosure, the adult stem cells may be mesenchymal stem cells derived from one or more tissues selected from the group consisting of an umbilical cord, umbilical cord blood, bone marrow, fat, muscle, nerve, skin, an amniotic membrane, and a placenta.

Another aspect of the present disclosure provides a method for enhancing the proliferation of stem cells, which comprises culturing stem cells in the medium composition.

Still another aspect of the present disclosure provides stem cells having an enhanced proliferation capability, which are obtained by the method.

According to one embodiment of the present disclosure, the stem cells may be mesenchymal stem cells derived from one or more tissues selected from the group consisting of an umbilical cord, umbilical cord blood, bone marrow, fat, muscle, nerve, skin, an amniotic membrane, and a placenta.

Advantageous Effects

According to the present disclosure, next-generation high-efficiency stem cells can be mass-produced through a simple and safe method of controlling a culturing environment without using genetic modification or viral vectors, etc.

According to the present disclosure, a new methodology for developing high-efficiency stem cells can also be proposed by identifying a molecular biological mechanism and a metabolic regulation marker, which can selectively regulate the metabolic processes of stem cells.

BRIEF DESCRIPTION OF THE DRAWINGS

FIGS. 1A and 1B illustrate the results of a BrdU assay for verifying that the proliferation of human mesenchymal stem cells is enhanced by treatment with ethionamide, wherein FIG. 1A shows the results of comparison of proliferation rates of human umbilical cord mesenchymal stem cells according to the treatment concentration of ethionamide, and FIG. 1B shows results of comparison of proliferation rates of human umbilical cord mesenchymal stem cells according to the treatment time of ethionamide.

FIGS. 2A and 2B illustrate the results of flow cytometry for verifying that a human mesenchymal stem cell surface antigen is expressed by treatment with ethionamide, wherein FIG. 2A shows the results of comparison of expression patterns of a positive marker of human mesenchymal stem cells for the control cultured and not treated with ethionamide and human umbilical cord mesenchymal stem cells (ethionamide-primed MSCs) cultured and treated with ethionamide, and FIG. 2B shows the results of comparison of expression patterns of a negative marker (FIG. 2B) of human mesenchymal stem cells for the control cultured and not treated with ethionamide and human umbilical cord mesenchymal stem cells (ethionamide-primed MSCs) cultured and treated with ethionamide.

FIGS. 3A, 3B and 3C illustrate the results of verifying the differentiation potency of human mesenchymal stem cells by treatment with ethionamide, wherein FIG. 3A shows the results of differentiation efficiency of the control, which has been cultured and not treated with ethionamide, and human umbilical cord mesenchymal stem cells (ethionamide-primed MSCs), which have been cultured and treated with ethionamide, into adipocytes, FIG. 3B shows the results of differentiation efficiency of the control, which has been cultured and not treated with ethionamide, and human umbilical cord mesenchymal stem cells (ethionamide-primed MSCs), which have been cultured and treated with ethionamide, into aosteocytes, and FIG. 3C shows the results of differentiation efficiency of the control, which has been cultured and not treated with ethionamide, and human umbilical cord mesenchymal stem cells (ethionamide-primed MSCs), which have been cultured and treated with ethionamide, into chondrocytes.

DETAILED DESCRIPTION

Figure 1A:
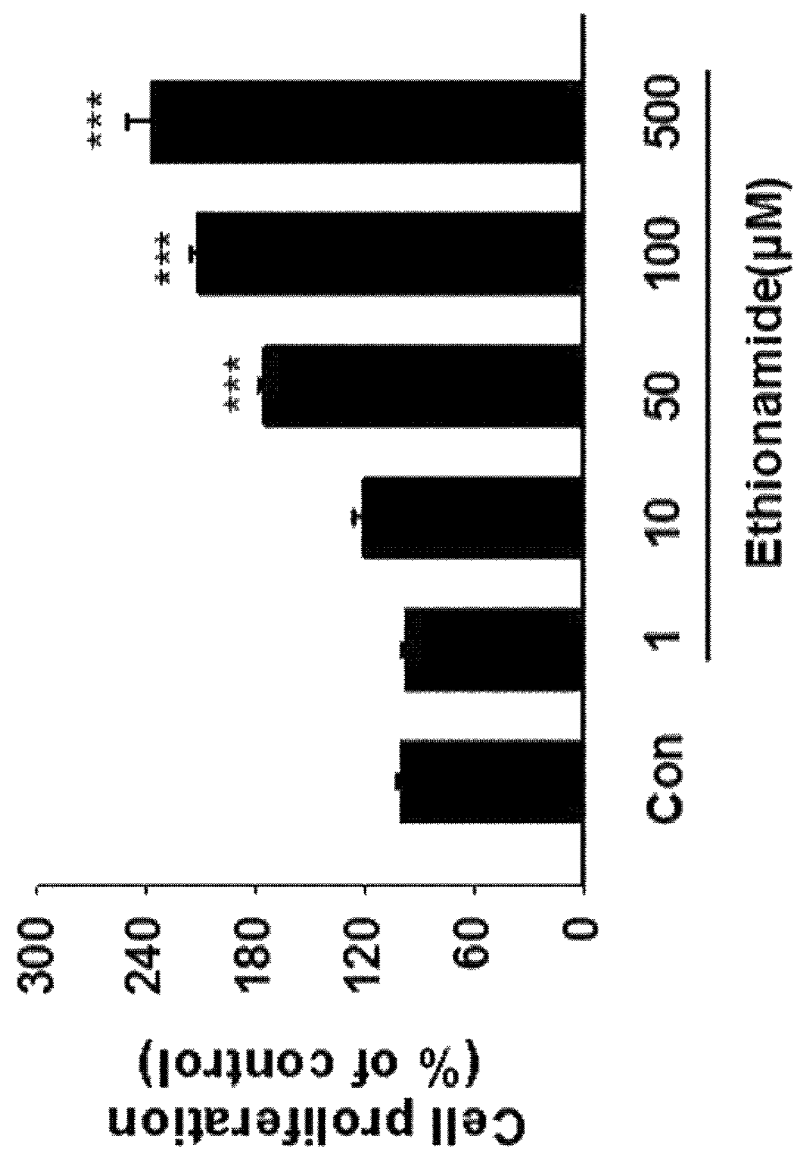

The present disclosure provides a medium composition for enhancing the proliferation of stem cells, which includes ethionamide.

In the prior art, although ethionamide (2-ethylpyridine-4-carbothioamide) is a thionamide-based antibiotic that is known to be used to treat infectious diseases infected caused by bacteria, the use of ethionamide according the present disclosure was first found to improve proliferation.

[Ethionamide]

The present inventors have identified an ability to enhance the proliferation of stem cells when the stem cells are treated with ethionamide according to specific embodiments.

In one embodiment of the present disclosure, it was confirmed that when the mesenchymal stem cells are cultured in a medium treated with various concentrations, that is, a concentration of 1, 10, 50, 100, and 500 uM, of ethionamide, the proliferation of human umbilical cord mesenchymal stem cells was significantly enhanced at a treatment concentration of 50 uM or more and it was also confirmed that ethionamide has the highest effect of enhancing proliferation when the mesenchymal stem cells are treated with ethionamide for 72 hours (see Example 2).

In another embodiment of the present disclosure, by analyzing a surface antigen expression pattern of the human umbilical cord mesenchymal stem cells cultured and treated with ethionamide, it was confirmed that the expression pattern is identical to that of the control which is not treated with ethionamide. Also, by being induced to differentiate into adipocytes, osteocytes, and chondrocytes, it was confirmed that characteristics of the mesenchymal stem cells are well retained based on the fact that the differentiation potency of the mesenchymal stem cells is not different from that of the control (see Examples 3 and 4).

The results show that ethionamide effectively enhances the proliferation of the mesenchymal stem cells while intactly retaining the characteristics of the mesenchymal stem cells when the mesenchymal stem cells are treated with ethionamide.

In the present disclosure, the concentration of ethionamide included in the medium is not limited, but ethionamide may be preferably included at a concentration of 1 to 500 uM, and more preferably a concentration of 50 to 500 uM. Further preferably, ethionamide may be included at a concentration of 100 uM.

In the present disclosure, although there is no limitation on the medium used for cell culture, it may be, for example, preferably an α-minimum essential media (α-MEM) medium supplemented with fetal bovine serum (FBS) and gentamicin. More preferably, the fetal bovine serum may be included at an amount of 10%, and the gentamicin may be included at a concentration of 50 ug/m L.

In the present disclosure, the term "stem cells" refer to cells that have a self-replicating ability as undifferentiated cells and also have an ability to differentiate into two or more different types of cells. The stem cells of the present disclosure may be autologous or allogeneic stem cells, and may be derived from any types of animals including humans and non-human mammals. In this case, the stem cells may be derived from an adult or derived from an embryo, but the present disclosure is not limited thereto.

The stem cells of the present disclosure include embryonic stem cells or adult stem cells, and preferably include adult stem cells. The adult stem cells may be mesenchymal stem cells, human tissue-derived mesenchymal stromal cells, human tissue-derived mesenchymal stem cells, multipotent stem cells, or amniotic epithelial cells, and may be preferably mesenchymal stem cells, but the present disclosure is not limited thereto. The mesenchymal stem cells may be mesenchymal stem cells derived from an umbilical cord, umbilical cord blood, bone marrow, fat, muscle, nerve, skin, an amniotic membrane, and a placenta, but the present disclosure is not limited thereto.

In the present disclosure, the term "umbilical cord-derived stem cells (Wharton's Jelly-derived stem cells)" include all types of stem cells isolated from the umbilical cord, and may refer to a cord that connects the baby's abdomen to a pregnant mother so that a mammalian fetus can grow. In general, the umbilical cord-derived stem cells may refers to a tissue consisting of three blood vessels, that is, two umbilical arteries and one umbilical vein, all of which are surrounded by the Wharton's jelly.

In the present disclosure, the term "placenta-derived stem cells" include all types of stem cells isolated from the placenta, and preferably include four types of stem cells isolated from the human placenta separated from the body, that is, (1) human amniotic epithelial cells (hAECs), (2) human amniotic mesenchymal stromal cells or human amniotic mesenchymal stem cells (hAMSCs)), 3) human chorionic mesenchymal stromal cells or human chorionic mesenchymal stem cells (hCMSCs)), and (4) human chorionic trophoblastic cells (hCTCs).

The isolation of the mesenchymal stem cells may be performed using methods obvious to those skilled in the art. For example, the mesenchymal stem cells may be isolated using methods disclosed in Pittenger, et al., Science 284: 143, 1997, and Van et al., J. Clin. Invest., 58: 699, 1976.

In the present disclosure, the term "enhancing proliferation of stem cells" encompasses a meaning of retaining stem cell characteristics by suppressing cell aging and improving cell proliferation capability and protein homeostasis. As a result, expression of a Nanog, Oct4 or KLF4 gene as a stem cells marker may increase. These genes are known to be genes that play an important role in retaining stem cell characteristics, that is, the pluripotency of stem cells which are mainly expressed in embryonic stem cells.

Also, the present disclosure provides a method for enhancing the proliferation of stem cells, which includes culturing the stem cells in the medium composition, and stem cells having an enhanced proliferation capability, which are obtained by the method.

Further, the present disclosure provides a cell therapeutic agent for treating various diseases, which includes the stem cells.

MODE FOR INVENTION

Hereinafter, preferred embodiments of the present disclosure are provided to aid in understanding the present disclosure. However, it should be understood that the following examples are merely intended to provide a better understanding of the present disclosure, and are not intended to limit the scope of the present disclosure.

EXAMPLES

Example 1: Preparation of Human Umbilical Cord Mesenchymal Stem Cells

Human umbilical cord mesenchymal stem cells were isolated according to the criteria approved by the Institutional Review Board (IRB; IRB #2015-09-023-003) of the Samsung Medical Center. That is, an umbilical cord was obtained, and mesenchymal stem cells were then isolated from the umbilical cord using the following method.

First, an umbilical cord tissue having a size of 3 to 4 cm was cut into pieces, and treated with a collagenase solution (Gibco, USA) for 60 to 90 minutes to degrade the extracellular matrix. Thereafter, 0.25% trypsin (Gibco, USA) was added thereto, and the umbilical cord tissue was digested at 37° C. for 30 minutes. Then, fetal bovine serum (FBS; Biowest, USA) was added thereto, and the resulting mixture was centrifuged at 1000×g for 10 minutes to obtain cells. The cells were then cultured in a minimum essential media (MEM) medium supplemented with 10% FBS and 50 ug/mL gentamicin (Gibco, USA) under a 37° C. and 5% $CO_2$ environment. The mesenchymal stem cells were passaged 5 or 6 times, and then used for this experiment.

Example 2: Confirmation of Enhancement of Proliferation of Human Mesenchymal Stem Cells To check a cell proliferation-enhancing effect according to the treatment with ethionamide, the human umbilical cord mesenchymal stem cells ($1 \times 10^4$ cells) prepared by the method of Example 1 were seeded in a 96-well plate, cultured for 24 hours, and then treated with various concentrations (1 to 500 μM) of ethionamide. After 72 hours, cell proliferation analysis was performed. For this purpose, a BrdU cell proliferation assay kit (Cell Signaling Technology, USA) using 5-bromo-2'-deoxyuridine (BrdU) bound during DNA synthesis in cells was used. Specifically, BrdU was added to cells, and reacted for 24 hours. Thereafter, the cells were immobilized, and DNA was denatured. Then, the cells were treated with an anti-BrdU antibody, and then reacted with a tetramethylbenzidine (TMB) substrate using a secondary antibody conjugated with horse-radish peroxidase (HRP), and an absorbance value was measured at 450 nm using an ELISA reader.

Figure 1B:
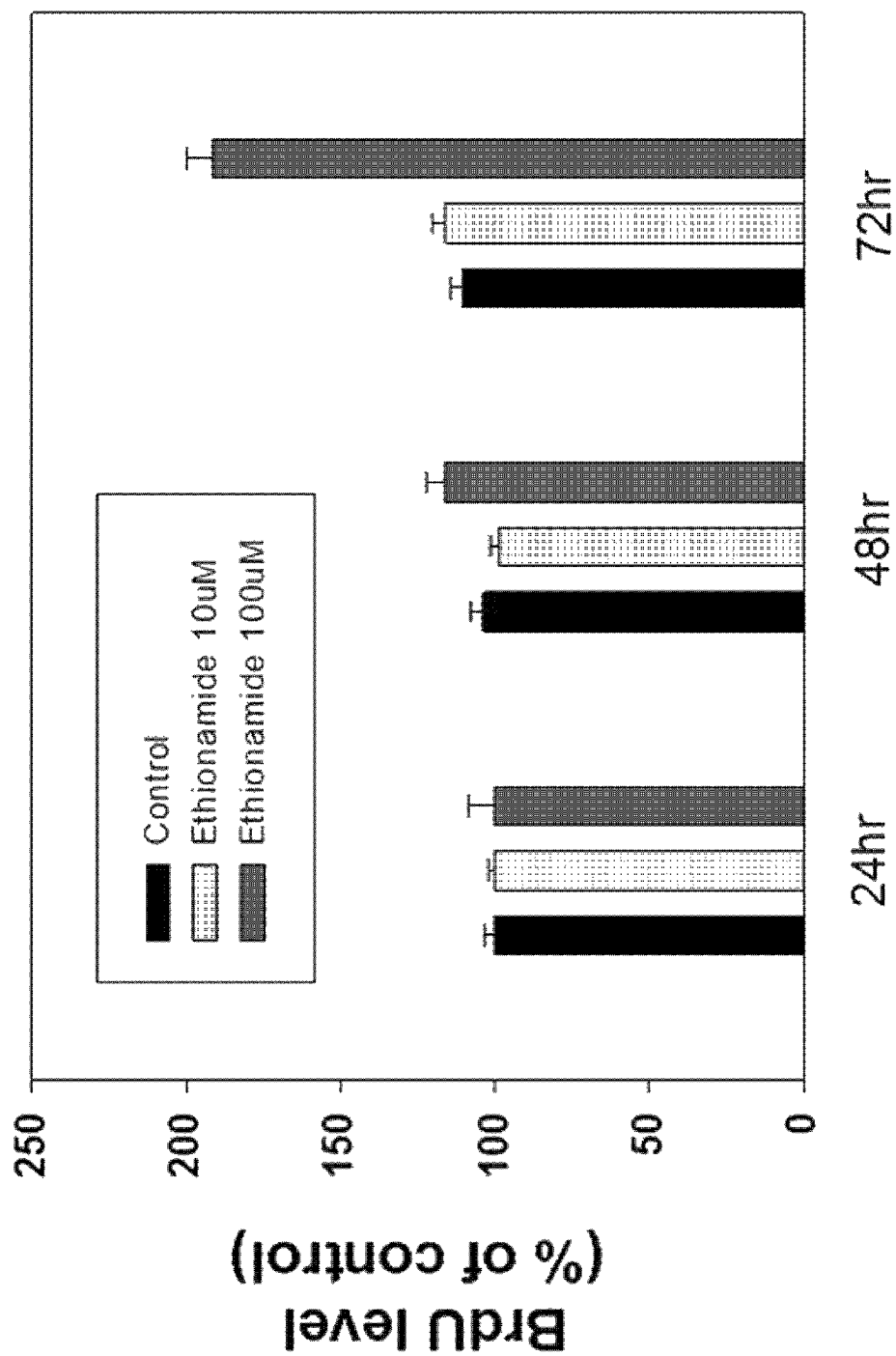

As a result, as shown in FIG. 1A, it was confirmed that a proliferation rate of the cells was significantly enhanced when the cells were treated with ethionamide at a concentration of 50 uM or more. Also, the cells were treated with 10 uM or 100 uM ethionamide, and proliferation efficiencies according to treatment time were compared. As a result, as shown in FIG. 1B, it was confirmed that the proliferation rate was most significantly enhanced when the cells were treated with ethionamide for 72 hours.

Example 3: Analysis of Cell Surface Antigen of Human Mesenchymal Stem Cells Treated with Ethionamide To check the characteristics of the human umbilical cord mesenchymal stem cells cultured and treated with the ethionamide drug, the expression of a surface antigen of the mesenchymal stem cells was observed using flow cytometry (fluorescence-activated cell sorting; FACS).

More specifically, the human umbilical cord mesenchymal stem cells ($2 \times 10^5$ cells) were equally divided into 1.5 ml microtubes, treated with 100 μL of phosphate-buffered saline (PBS) containing 2% FBS, treated with an antibody bound to fluorescein isothiocyanate (FITC), phycoerythrin (PE), or allophycocyanin (APC), and then reacted at room temperature for 20 minutes. In this Example, it was observed whether positive and negative markers were expressed using CD44, CD73, CD90, CD105, CD166, CD11b, CD14, CD19, CD34, CD45, and HLA-DR antibodies. After the reaction, an antibody reaction was neutralized with PBS containing 2% FBS, and it was then determined whether the positive and negative markers were expressed using a flow cytometer.

Figure 2A:
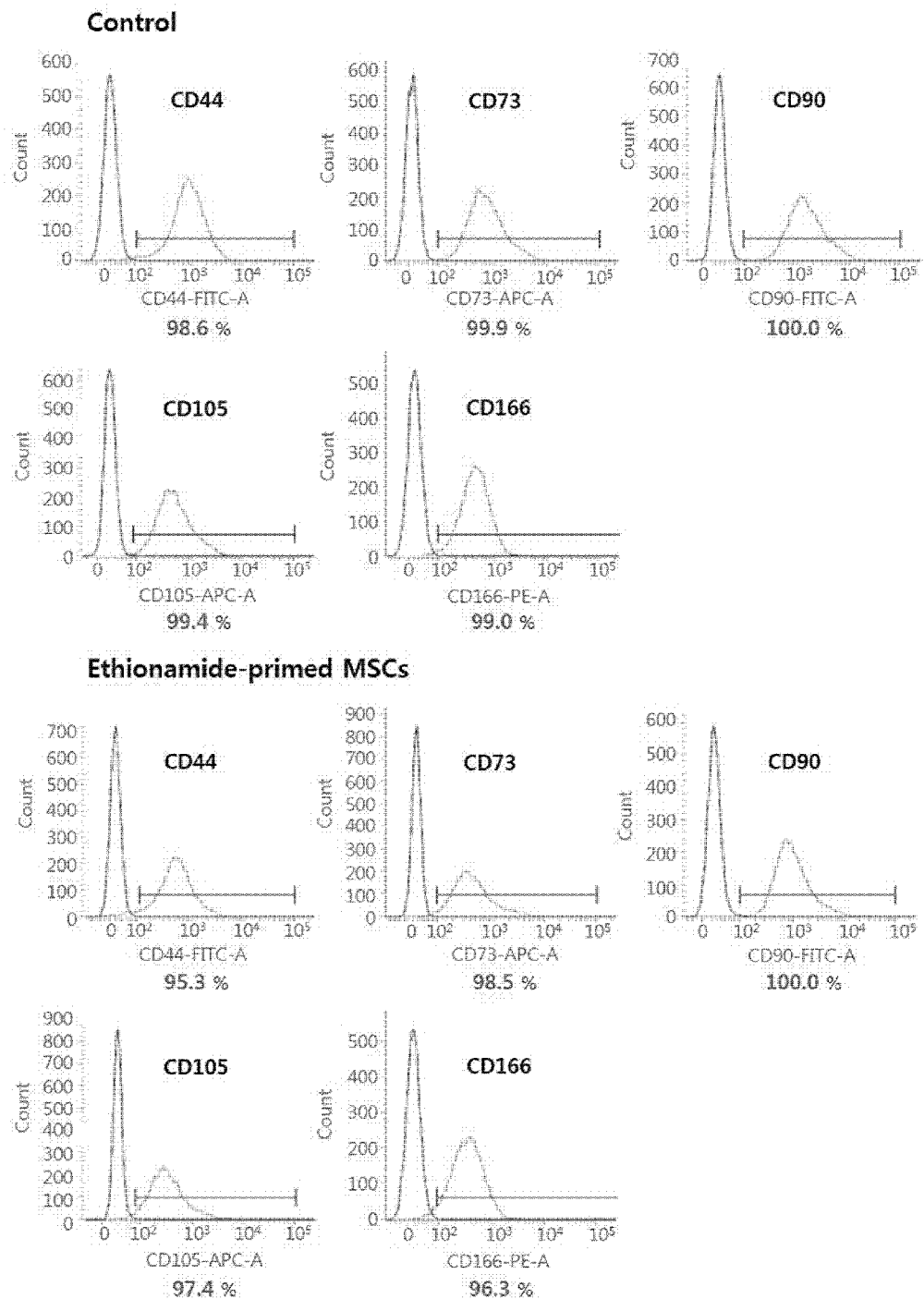
Figure 2B:
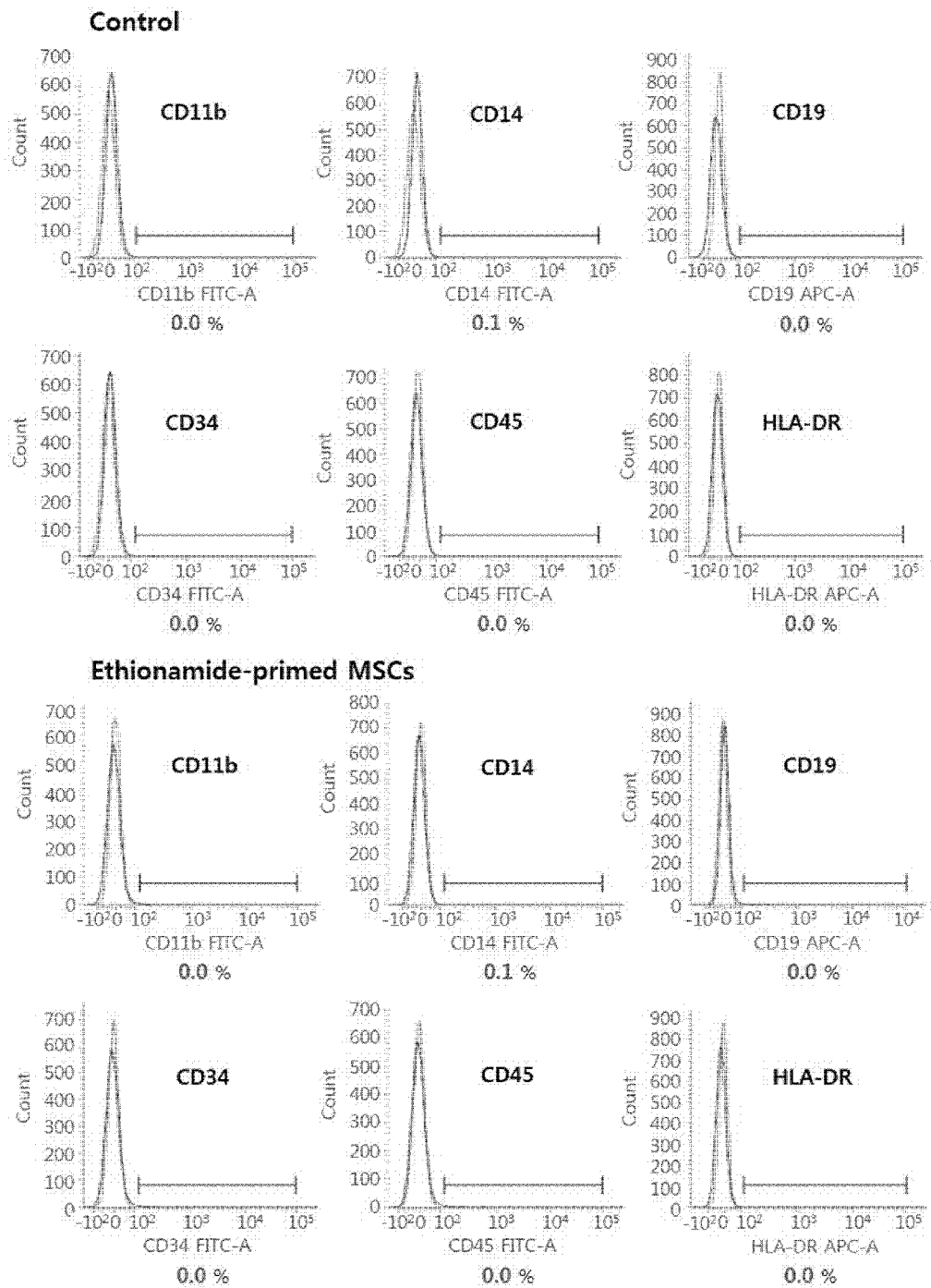

First, it was determined whether the positive markers CD44, CD73, CD90, CD105, and CD166 were expressed. As a result, as shown in FIG. 2A, it was confirmed that the markers were expressed at a similar level in the human mesenchymal stem cells (ethionamide-primed MSCs) cultured and treated with ethionamide, compared to the control cultured and not treated with ethionamide. Also, it was confirmed that the negative markers CD11b, CD14, CD19, CD34, CD45, and HLA-DR were not expressed at a level similar to the control.

From the results, it can be seen that the characteristics of the mesenchymal stem cells were well retained even when the mesenchymal stem cells were cultured after treatment with ethionamide.

Example 4: Analysis of Differentiation Potency of Human Mesenchymal Stem Cells Treated with Ethionamide In addition to the results of Example 3, to check whether the differentiation potency of the human umbilical cord mesenchymal stem cells cultured and treated with ethionamide was well retained, the mesenchymal stem cells were induced to differentiate into adipocytes, osteocytes, and chondrocytes, and degrees of differentiation were quantified.

Specifically, to induce differentiation into adipocytes or osteocytes, human umbilical cord mesenchymal stem cells ($1 \times 10^5$ cells) cultured in a medium treated with ethionamide were seeded in a 6-well plate, and the differentiation was induced for approximately 3 weeks using adipogenesis/osteogenesis differentiation kits (Gibco, USA) while replacing the medium with a fresh medium twice a week. Thereafter, the cells differentiated into adipocytes and osteocytes were stained with Oil red O and Alizarin Red S to check whether the cells were differentiated into adipocytes and osteocytes. Quantification of the adipocytes was carried out by completely removing the medium from differentiation culture containers, drying the culture containers, putting 100% isopropanol into the culture containers, culturing the cells at room temperature for 10 minutes, thoroughly mixing the differentiated cells with 100% isopropanol, and measuring an absorbance at 500 nm to quantify the degree of differentiation. Quantification of the osteocytes was carried out by quantifying the degree of differentiation using an Alizarin Red S staining quantification assay kit (ScienCell, USA).

Meanwhile, to induce differentiation into chondrocytes, $5 \times 10^5$ cells in the form of a pellet were put into a 15 mL tube, and differentiation of the cells was induced in a chondrocyte induction medium (high-glucose DMEM (Biowest, France), 100 nM dexamethasone (Sigma-Aldrich, USA), 50 mg/mL L-ascorbic acid (Sigma-Aldrich, USA), 100 mg/mL sodium pyruvate (Sigma-Aldrich, USA), 40 mg/mL L-proline (Sigma-Aldrich, USA), 10 ng/mL transforming growth factor β3 (TGF-β3, R&D Systems, USA), 500 ng/mL bone morphogenic protein 6 (BMP-6, R&D Systems, USA), and 50 mg/mL ITS+ premix (Becton Dickinson, USA)) for approximately 4 weeks. The cells differentiated into the chondrocytes were immobilized using an OCT compound (Tissue-Tek, USA), and then cut into slide sections having a thickness of 10 μm. Thereafter, the slide sections were stained with a 0.1% Safranin-O solution to check whether the cells were differentiated into chondrocytes. Also, quantification of the chondrocytes was carried out by quantifying a staining degree using an Image J analysis program (National Institutes of Health, USA).

Figure 3A:
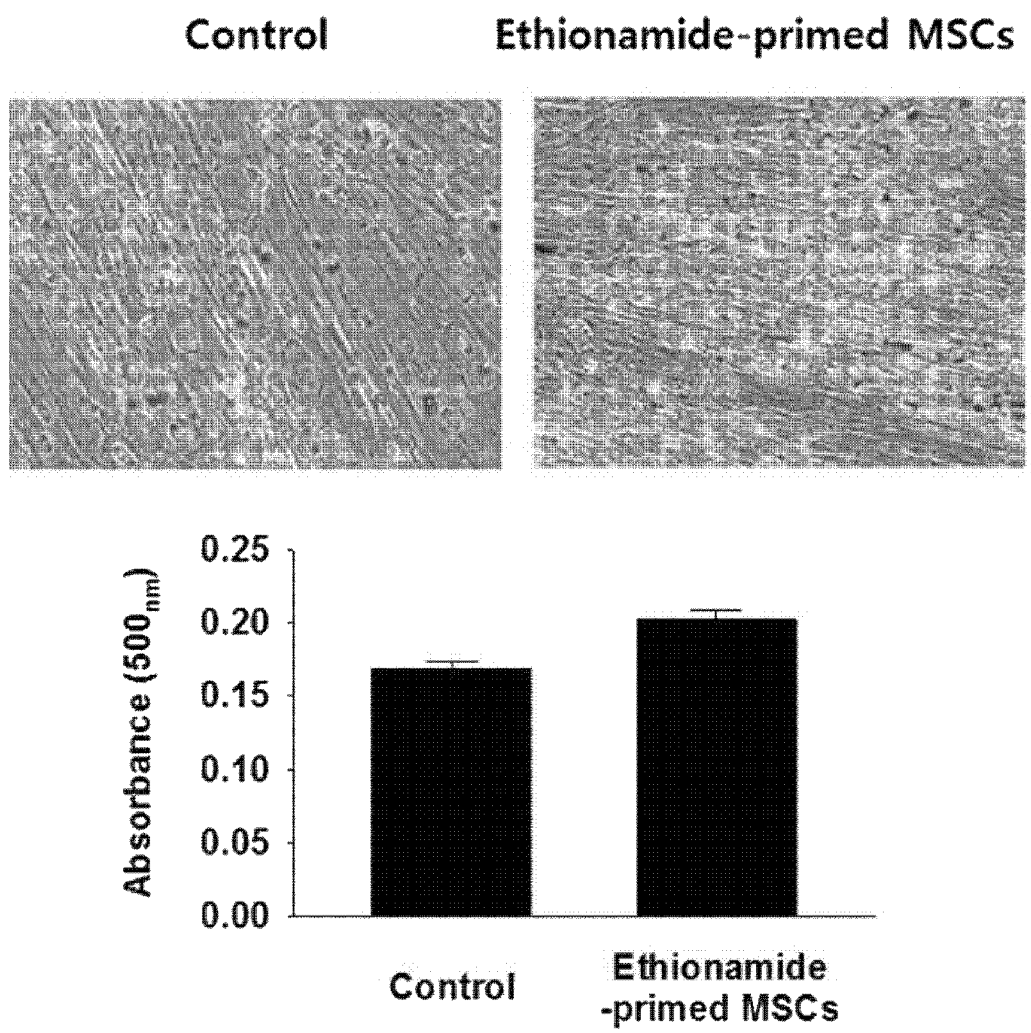
Figure 3B:
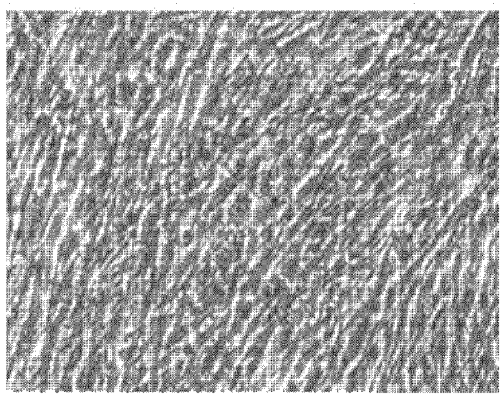
Figure 3B:
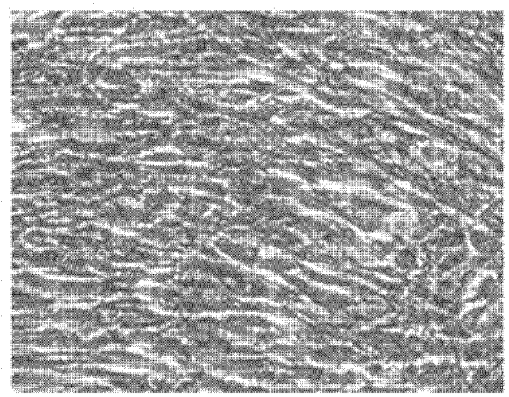
Figure 3B:
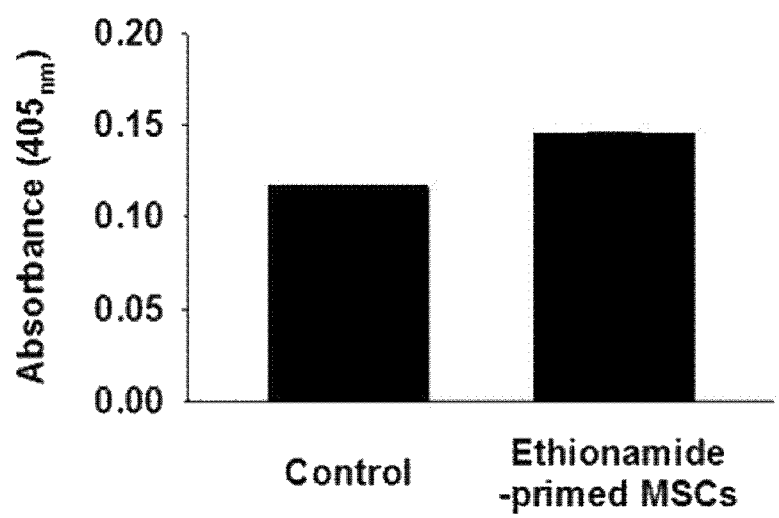
Figure 3C:
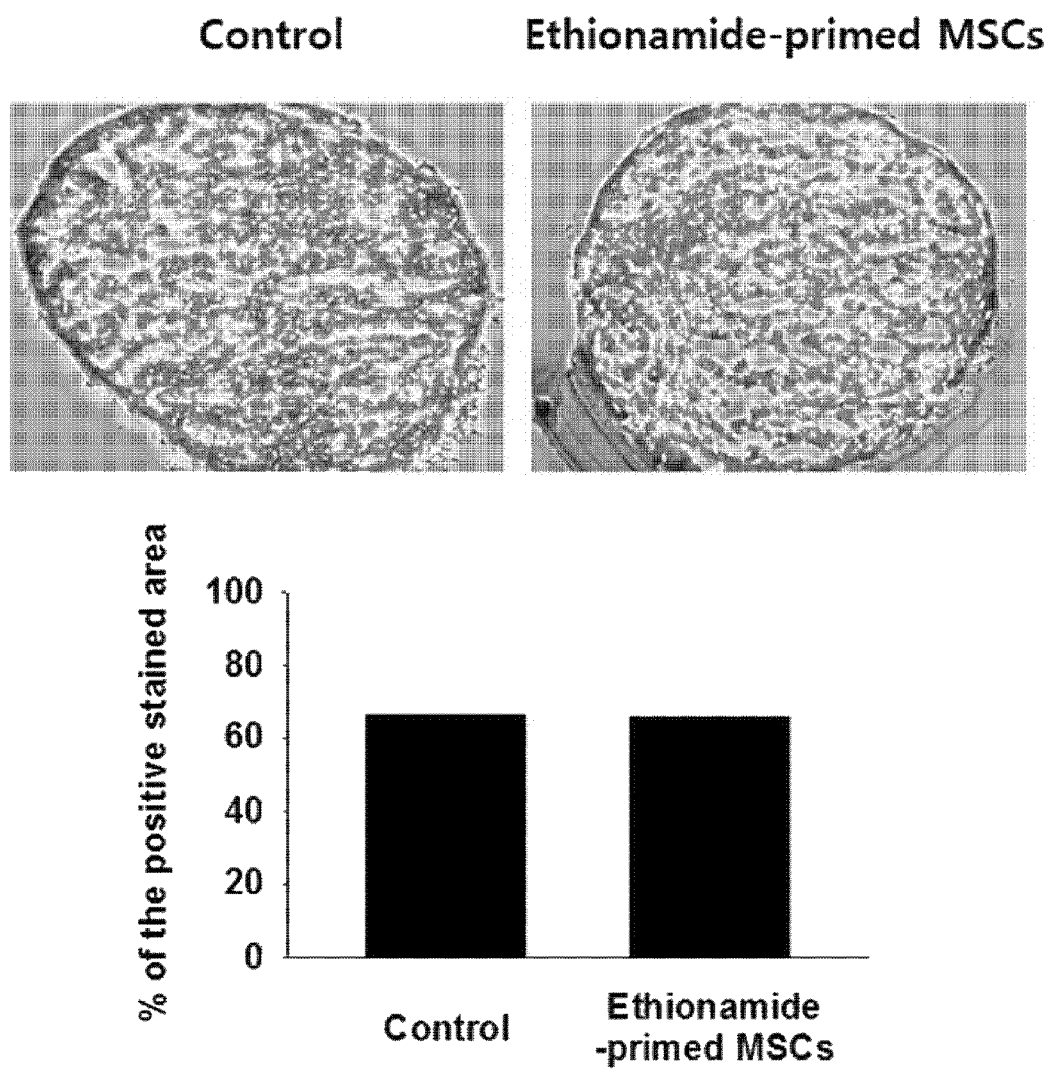

From the analysis results, as shown in FIGS. 3A to 3C, it was confirmed that the human umbilical cord mesenchymal stem cells (Ethionamide-primed MSCs) cultured and treated with ethionamide were well differentiated into adipocytes, osteocytes, and chondrocytes, compared to the control which was not treated with ethionamide.

From the results, it can be seen that the differentiation potency of the mesenchymal stem cells was well retained even when the mesenchymal stem cells were treated with ethionamide.

It will be apparent to those skilled in the art that various modifications can be made to the above-described exemplary embodiments of the present disclosure without departing from the scope of the invention. Thus, it is intended that the present disclosure cover all such modifications provided they come within the scope of the appended claims and their equivalents.

The above description of the present disclosure are given by way of illustration only, and it should be understood by those skilled in the art to which the present disclosure belongs that various changes and modifications can be made without departing from the technical spirit and scope of the present disclosure. Therefore, it should be understood that the aforementioned embodiments are given by way of illustration only, and are not intended to be limiting in all aspects.

INDUSTRIAL APPLICABILITY

The ethionamide according to the present disclosure effectively enhances the proliferation of human mesenchymal stem cells while intactly retaining the characteristics of the mesenchymal stem cells. Therefore, the ethionamide and the medium composition including the same are expected to be useful in securing a large amount of high-quality stem cells in fundamental research fields using the stem cells, and related industry fields such as development of therapeutic agents and cosmetics, and the like.

What is claimed is:
1. A method for enhancing the proliferation of adult stem cells, comprising:
    culturing adult stem cells in a medium composition comprising ethionamide for 72 hours,
    wherein the ethionamide is contained in the medium at 100 μM, and
    wherein the adult stem cells are mesenchymal stem cells derived from one or more tissues selected from the group consisting of an umbilical cord umbilical cord blood, bone marrow, fat, muscle, nerve, skin, an amniotic membrane, and a placenta.
2. The method of claim 1, wherein the medium is α-Minimum Essential Medium (α-MEM) supplemented with fetus bovine serum (FBS) and gentamicin.

* * * * *